(12) United States Patent
Flohr et al.

(10) Patent No.: US 10,824,857 B2
(45) Date of Patent: Nov. 3, 2020

(54) METHOD AND SYSTEM FOR THE CLASSIFICATION OF MATERIALS BY MEANS OF MACHINE LEARNING

(71) Applicant: Siemens Healthcare GmbH, Erlangen (DE)

(72) Inventors: Thomas Flohr, Uehlfeld (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 92 days.

(21) Appl. No.: 16/133,889

(22) Filed: Sep. 18, 2018

(65) Prior Publication Data

US 2019/0102621 A1 Apr. 4, 2019

(30) Foreign Application Priority Data

Oct. 2, 2017 (DE) .................... 10 2017 217 543

(51) Int. Cl.
*G06K 9/62* (2006.01)
*G06K 9/00* (2006.01)
(Continued)

(52) U.S. Cl.
CPC .......... *G06K 9/00536* (2013.01); *A61B 6/032* (2013.01); *A61B 6/482* (2013.01);
(Continued)

(58) Field of Classification Search
CPC ............. G06K 9/00536; G06K 9/6256; G06K 9/6262; G06K 2209/051; G06K 9/6267;
(Continued)

(56) References Cited

U.S. PATENT DOCUMENTS 10,037,601 B1* 7/2018 Ben-Ari ............... G06K 9/4604
2003/0215120 A1 11/2003 Uppaluri et al.
(Continued)

FOREIGN PATENT DOCUMENTS

CN 1504931 A 6/2004
CN 104751429 A 7/2015

OTHER PUBLICATIONS

German Office Action #102017217543.5 dated Aug. 1, 2018.
(Continued)

*Primary Examiner* — Dhaval V Patel
(74) *Attorney, Agent, or Firm* — Harness, Dickey & Pierce, P.L.C.

(57) ABSTRACT

A method is for creating a classification unit for the automatic classification of materials. An embodiment of the method includes provision of a learning computing device; provision of a start classification unit; provision of a reference image set including spectral reference recordings with annotated materials; and training of the classification unit with the reference recording set. Furthermore, a classification method is for the automatic classification of materials in an image recording. An embodiment of the classification method includes provision of a trained classification unit; provision of a spectral image recording; examination of the image recording for materials via the classification unit; and identification of the determined materials. Furthermore, a classification unit, a learning computing device, a control device and a medical imaging system are disclosed.

22 Claims, 5 Drawing Sheets

(51) Int. Cl.
  *A61B 6/00* (2006.01)
  *A61B 6/03* (2006.01)
  *G06T 7/11* (2017.01)
  *G06N 20/00* (2019.01)
  *G06T 7/00* (2017.01)

(52) U.S. Cl.
  CPC .......... *A61B 6/5217* (2013.01); *A61B 6/5294* (2013.01); *G06K 9/6256* (2013.01); *G06K 9/6262* (2013.01); *G06N 20/00* (2019.01); *G06T 7/0014* (2013.01); *G06T 7/11* (2017.01); *A61B 6/4241* (2013.01); *G06K 2209/051* (2013.01); *G06T 2207/10081* (2013.01); *G06T 2207/20081* (2013.01)

(58) Field of Classification Search
  CPC ....... A61B 6/482; A61B 6/032; A61B 6/5217; A61B 6/5294; A61B 6/4241; G06T 7/0014; G06T 2207/20081; G06T 2207/10081; G06N 20/00; G16H 30/20
  See application file for complete search history.

(56) References Cited

U.S. PATENT DOCUMENTS

| | | |
|---|---|---|
| 2011/0188715 A1 | 8/2011 | Shotton et al. |
| 2014/0201126 A1* | 7/2014 | Zadeh .................. A61B 5/4803 706/52 |
| 2016/0123904 A1* | 5/2016 | Masood ............... G01N 23/046 382/131 |

OTHER PUBLICATIONS

German Office Action and English translation thereof dated Aug. 1, 2018.

German Decision to Grant and English translation thereof dated Sep. 30, 2019.

Li, Chao et al. "Differentiating Pancreatic Mucinous Cystic Neoplasms Form Serous Oligocystic Adenomas in Spectral CT Images Using Machine Learning Algorithms: A Preliminary Study"; Proceedings of the 2013 International Conference on Machine Learning and Cybernetics; 2013.

Chinese Office Action and English translation thereof dated Mar. 10, 2020.

* cited by examiner

METHOD AND SYSTEM FOR THE CLASSIFICATION OF MATERIALS BY MEANS OF MACHINE LEARNING

The present application hereby claims priority under 35 U.S.C. § 119 to German patent application number DE 102017217543.5 filed Oct. 2, 2017, the entire contents of which are hereby incorporated herein by reference.

FIELD

Embodiments of the invention generally relate to a method for creating a classification unit for the automatic classification of materials in a spectral medical image recording and/or a classification unit and a learning computing device for this purpose.

Furthermore, embodiments of the invention generally relate to a classification method for the automatic classification of materials in a spectral medical image recording using such a classification unit, a control device for the control of a medical imaging system and a corresponding medical imaging system. Within the scope of embodiments of the invention, an image recording is a digital image and therefore comprises image data and/or it consists of image data.

BACKGROUND

Imaging methods in medicine usually rely upon the evaluation of a single measured variable and/or a single physical measuring principle for the creation of each pixel of an image recording. Thus, for example, computer tomography ("CT") detects the local X-ray attenuation of the patient as the only measured variable. Chemically distinct materials which have the same local X-ray attenuation due to different concentrations, for example, are shown in a CT image with the same CT value (normally in Hounsfield units HU) and therefore cannot be distinguished from one another in the image.

This is problematic in many CT applications. An example is the separation of bones and contrast agent-filled vessels in CT angiographies. The iodine in the blood may have the same X-ray absorption as the surrounding bone such that vessels and bones particularly in complicated anatomical situations, for example, in the base of the skull, can only be shown individually and separately with difficulty. Another example is the more precise characterization of kidney stones. Stones containing calcium and stones containing uric acid may display the same X-ray absorption. They therefore cannot be distinguished in the CT image, but have different treatment options. Another example is the distinction of gout crystals from other deposits on the joints.

Sometimes radiation in two or more energy ranges is used to classify different substances ("materials") in the tissue. For example, a recording of CT images with two or more different X-ray energies ("Dual Energy CT", "Spectral CT") can be used to distinguish different materials.

The X-ray absorption of materials found in the body in the energy range of CT-typical X-radiation (30-150 keV) is determined by two physical mechanisms, the photoelectric and the Compton effect. These mechanisms have different energy dependence and their relative share of the total X-ray absorption depends on the respective material, more precisely on its atomic number and its density.

Due to the presence of two physical effects with different energy dependence, two materials can be distinguished by way of recordings with two or more different X-ray energies. If additional materials with a K-edge in the relevant energy range, for example, gadolinium, gold or iron, are added, more than two materials can also be separated using recordings with more than two X-ray energies.

A recording of CT images with several different X-ray energies is possible, for example, with Dual Source CT devices with operation of both tubes with different voltages, Single Source CT devices with switching of the tube voltage, CT devices with separated pre-filtering ("Twin Beam"), CT devices with Dual Layer detectors or CT devices with photon-counting detectors. However, other medical imaging devices which are not based on the principle of a computer tomograph can also enable material classification using two recording energies.

As a rule, separation is based on the determination of a "spectral variable" which characterizes the material-dependent change in X-ray absorption with the different X-ray energies. Such a spectral variable is, for example, the so-called Dual Energy Ratio, which is the X-ray attenuation value at a low X-ray energy A divided by the X-ray attenuation value at a higher energy B. If there were no spectral effects, the Dual Energy Ratio would be equal to 1. The more marked the spectral effect is for the respective material, the more the Dual Energy Ratio deviates from 1. As a rule, a certain constant limit value of the spectral variable is used for the material separation of two materials A and B. Whether the spectral variable is below the limit value at this point, when it is material A, is investigated for each pixel in the CT image. If the spectral variable is above the limit value, then it is material B.

SUMMARY

The inventors have discovered that a disadvantage of the known systems is that the quality of material separation in recordings with several energies is impaired by certain error sources. Thus, for example, the images are noisy, and individual pixels may exhibit a false value of the spectral variable as a result of the presence of image noises which can lead to a false material classification. This is the case, for example, in applications for the automatic removal of bones from CT angiographic images where areas of the bone are erroneously classified as contrast agent and thus remain in the image while areas of the vessels, particularly with lower contrast agent density or a small vessel diameter, are erroneously classified as bones and are thus removed from the image.

Furthermore, they have discovered that the quality of material separation depends on the form of the spectral variable and this in turn may vary greatly for individual CT technologies for the recording of spectral images. In particular, for CT devices with separated pre-filtering or for CT devices with Dual Layer detectors, only lower spectral effects are obtained such that clean material separation is not always ensured.

In at least one embodiment of the present invention, an alternative more convenient method is provided for classification; and in at least one embodiment, a corresponding classification unit and a control device are provided for the automatic control of a medical imaging system with which at least one of the disadvantages described above are avoided or at least reduced and with which different materials can be automated and reliably detected. Likewise, at least one embodiment relates to the creation of such a classification unit and corresponding computing devices.

Embodiments are directed to a method, a classification unit, a learning computing device, a classification method, a control device and an imaging medical system.

In at least one embodiment, a method is for creating a classification unit for the automatic classification of materials in a spectral medical image recording of an object. In at least one embodiment, the method comprises:

provisioning a learning computing device, designed to recognize graphic elements in image recordings via an algorithm;

provisioning a start classification unit, on or at the learning computing device, trainable via machine learning;

provisioning a reference recording set including spectral reference recordings of the object, materials to be classified being annotated in the spectral reference recordings of the object; and training the classification unit according to at least one principle of machine learning, for automatic classification of materials in thespectral medical image recording of the object, using the materials annotated in the spectral reference recordings.

A classification unit according to at least one embodiment of the invention for the automatic classification of materials in a spectral medical image recording of an object, as a rule recorded by via a medical imaging system, is produced using a method according to at least one embodiment of the invention. The classification unit according to at least one embodiment of the invention was therefore produced according to the principle of machine learning from a start classification unit, wherein training was based on the recognition of materials in reference images of a reference recording set provided. Recognition took place by way of the recognition algorithm by way of a learning computing device provided which had a start classification unit which was trained.

At least one embodiment of the invention is directed to a classification unit for automatic classification of materials in a spectral medical image recording of an object, comprising:

a memory storing program computer-readable instructions; and one or more processors configured to execute the instructions such that the one or more processors are configured to, recognize graphic elements in image recordings via an algorithm;

provision a reference recording set including spectral reference recordings of the object, materials to be classified being annotated in the spectral reference recordings of the object; and train the classification unit according to at least one principle of machine learning, for the automatic classification of materials in the spectral medical image recording of the object, using the materials annotated in the spectral reference recordings.

A learning computing device according to at least one embodiment of the invention comprises a processor and a data storage device with instructions which, during execution thereof, enable the processor to collect reference images made available to the computing device, to detect materials in the reference images (as computer-intelligible data objects), and to train a start classification unit according to the method according to at least one embodiment of the invention.

At least one embodiment of the invention is directed to a learning computing device, comprising:

a processor; and a data storage device storing program computer-readable instructions which, during execution, enable the processor to:

record reference recordings provided as image data of an object, recognize materials in the reference recordings, the reference recordings including spectral reference recordings, materials to be classified being annotated in spectral reference recordings of the object, and graphic elements in the image data being recognizable via an algorithm, and train a classification unit according to at least one principle of machine learning, for automatic classification of materials in spectral medical image recording of the object, using the materials annotated in the spectral reference recordings.

At least one embodiment of the invention is directed to a classification method, comprising:

Provisioning or producing a classification unit trained via the method of claim 1;

provisioning a spectral medical image recording of an object;

classifying materials in the spectral medical image recording via the classification unit; and identifying at least one of the materials classified and material-specific processing of the spectral medical image recording.

A control device according to at least one embodiment of the invention for a medical imaging system is designed to perform a classification method according to at least one embodiment of the invention.

A control device according to at least one embodiment of the invention is designed for control of a medical imaging system, designed for performance of a classification method, comprising:

a processor; and a data storage device storing program computer-readable instructions which, during execution, enable the processor to provision or produce a classification unit trained via a method including recognizing graphic elements in image recordings via an algorithm, provisioning a reference recording set including spectral reference recordings of the object, materials to be classified being annotated in the spectral reference recordings of the object, and training the classification unit according to at least one principle of machine learning, for the automatic classification of materials in the spectral medical image recording of the object, using the materials annotated in the spectral reference recordings;

provisioning a spectral medical image recording of an object;

classifying materials in the spectral medical image recording via the classification unit; and identifying at least one of the materials classified and material-specific processing of the spectral medical image recording.

A medical imaging system according to at least one embodiment of the invention comprises a control device according to at least one embodiment of the invention.

At least one embodiment of the invention is also directed to a corresponding computer program product including a computer program which can be loaded directly into a storage device of a control device and/or a computing system, including program sections, to execute the method according to at least one embodiment of the invention when the program is executed. In addition to the computer program, such a computer program product may optionally comprise additional components such as, for example, documentation and/or additional components and also hardware components such as, for example, hardware keys (dongles, etc.) for the use of the software.

For transport to the control device and/or to the computing system and/or for storage on or in the control device and/or the computing system, at least one embodiment of the invention is directed to a non-transitory machine-readable medium in the form of the computer program product of at least one embodiment, for example, a memory stick, a hard disk or another portable or integral data carrier can be used on which the program sections of the computer program which can be read in and executed by a processor unit are stored. The processor unit may, for example, have one or more cooperating microprocessors or the like.

BRIEF DESCRIPTION OF THE DRAWINGS

The invention is explained again in more detail hereinafter with reference to the attached figures on the basis of example embodiments. In the various figures, the same components are provided with identical reference characters. As a rule, the figures are not to scale. In the figures.

In the following explanations, it is assumed that the medical imaging system and/or imaging system is a computer tomography system. In principle, however, the method can also be used in other imaging systems.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The solution of the problem described above is highly complex and a classification of materials not possible in a simple manner. Nor can a classification unit according to at least one embodiment of the invention be produced in a simple manner. At least one embodiment of the invention therefore comprises not only the classification unit and/or a method for the classification of materials with this classification unit, but also the production of this classification unit and the associated computing device. At the same time, classification also offers the opportunity of eliminating materials controlling an imaging medical device so that when an erroneous material classification is detected, it immediately makes a second image recording with other recording parameters to obtain a correct classification of different materials. This is also part of at least one embodiment of the invention.

The method according to at least one embodiment of the invention serves to create a classification unit for the automatic classification of materials in a spectral medical image recording of an object. Spectral image recordings are known in the context of medicine and refer to image recordings which have been produced with at least two recording energies. They usually comprise image data for two partial images, a partial image for the first receiving energy and a partial image for a second receiving energy. Often these partial images are referred to in accordance with the voltage at the X-ray source for the adjustment of the receiving energy as "High kV" (High Kilovolt sometimes also as "High keV": High kiloelectronvolt) and "Low kV" (Low Kilovolt; and/or "Low keV").

Both reconstructed recordings as well as raw data sets can be used for the image recordings, for example, spectral CT raw data sets or CT images reconstructed thereof.

In at least one embodiment, a method comprises:

Provision of a Learning Computing Device.

Such a learning computing device is described in more detail below. The learning computing device is designed to detect graphic elements in the image recording and/or in the image data of the image recordings via an algorithm (also referred to as a "recognition algorithm"). Graphic elements are here understood to mean, for example, patterns, graphical primitives and/or coherent areas or structures or the like. These may also include, for example, more complex structures such as, for example, organs, bones, vessels etc.

Provision of a Start Classification Unit.

The start classification unit is the subsequent classification unit which has not yet been trained and/or not yet optimally trained, however. It is provided on the learning computing device and is designed to be trained via machine learning (by the computing device). The recognition algorithm can also be, for example, part of the (start) classification unit itself.

Provision of a Reference Recording Set.

This reference recording set can be provided by way of an image data library which can also be referred to as a "reference library". The reference recording set comprises spectral reference images which can be real images of an imaging medical system or artificially generated images. The reference images are image recordings and therefore comprise image data and/or consist of image data. The image data library may, for example, be a database with a set of reference images which are connected to the learning computing device via data technology. A suitable medical imaging system for the recording of spectral reference recording can, for example, be a computer tomograph ("CT").

In the reference images, the materials to be classified and if applicable, also object classifications such as, for example, the object classification "kidney stone", are advantageously annotated. The reference images are also "labeled" regarding materials. For example, in reference images an annotation of bones and vessels or an annotation of stones including the type of stone, or a correct annotation of gout crystals may be present.

Training of the Classification Unit.

The classification unit is trained according to a principle of machine learning based on a recognition of the materials of the reference images of the reference recording set of the image data library. Recognition takes place via the recognition algorithm.

The formulation used below and hereinafter "of an image recording (of a medical imaging system)" is here understood to mean an image recording of an object, for example, an organ, body part and/or area of a patient, (also referred to as a "motive") which has been produced via a medical imaging system. This may involve two-dimensional images and/or image data, volume image data or an image data set of a plurality of image data, for example, a stack of two-dimensional image data.

As image areas with a particular material cannot usually be comprehended by a computer, this elucidation is highlighted by the designation "data object". A "data object" is an image area which can be comprehensively recognized by a computer as a particular material.

A classification unit according to at least one embodiment of the invention for the automatic classification of materials in a spectral medical image recording of an object, as a rule recorded by vai a medical imaging system, is produced using a method according to at least one embodiment of the invention. The classification unit according to at least one embodiment of the invention was therefore produced according to the principle of machine learning from a start classification unit, wherein training was based on the recognition of materials in reference images of a reference recording set provided. Recognition took place by way of the recognition algorithm by way of a learning computing device provided which had a start classification unit which was trained.

A learning computing device according to at least one embodiment of the invention comprises a processor and a data storage device with instructions which, during execution thereof, enable the processor to collect reference images made available to the computing device, to detect materials in the reference images (as computer-intelligible data objects), and to train a start classification unit according to the method according to at least one embodiment of the invention.

A classification method according to at least one embodiment of the invention for the automatic classification of materials in a spectral medical image recording, particularly CT recordings or projection data, for example, dual-energy topograms, comprises:

Provision of a Classification Unit.

This classification unit is trained as described above. In this context, in particular it is first possible to also perform training of a start classification unit.

Provision of an Image Recording.

This image recording is a spectral medical image recording which, for example, has been recorded via a medical imaging system. For example, this image recording comprises High-kV and Low-kV data of a dual energy CT, as raw data or in the form of reconstructed image data.

Classification of Materials.

This classification of materials in image recording takes place via the classification unit.

Identification of the Classified Materials.

The materials can be simply identified with markers. However, material objects can also be inserted at the positions concerned and computer-intelligible elements added to the resulting image. Identification can be undertaken directly in the image recording or in an additional representation, for example of an additional image plane.

Alternatively, or in addition thereto, a material-specific processing of the image recording can be performed, for example, an elimination or at least reduction of determined materials. For example, the automatic removal of bone material from CT angiographic images could be performed.

In this manner, for example error sources as a result of image noises can be reduced by training the classification unit with a large quantity of appropriate data sets, and thus improving the quality of material separation beyond the normal level achieved with purely spectral methods.

A control device according to at least one embodiment of the invention for a medical imaging system is designed to perform a classification method according to at least one embodiment of the invention.

A medical imaging system according to at least one embodiment of the invention comprises a control device according to at least one embodiment of the invention.

The majority of the aforementioned components, in particular the classification unit, can be implemented wholly or in part in the form of software modules of a processor of a corresponding control device or a computing system. A largely software-based realization has the advantage that control devices and/or computing systems already used can also be upgraded easily via a software update in order to operate in the manner according to at least one embodiment of the invention.

In this respect, at least one embodiment of the invention is also directed to a corresponding computer program product including a computer program which can be loaded directly into a storage device of a control device and/or a computing system, including program sections, to execute the method according to at least one embodiment of the invention when the program is executed. In addition to the computer program, such a computer program product may optionally comprise additional components such as, for example, documentation and/or additional components and also hardware components such as, for example, hardware keys (dongles, etc.) for the use of the software.

For transport to the control device and/or to the computing system and/or for storage on or in the control device and/or the computing system, at least one embodiment of the invention is directed to a non-transitory machine-readable medium in the form of the computer program product, for example, a memory stick, a hard disk or another portable or integral data carrier can be used on which the program sections of the computer program which can be read in and executed by a processor unit are stored. The processor unit may, for example, have one or more cooperating microprocessors or the like.

A classification unit in the form of a computer program product is therefore also preferred with a computer program which can be loaded directly into a storage device of a computing system or a control device of a medical imaging system, with program sections to execute all the steps of the classification method according to at least one embodiment of the invention when the computer program is executed in the computing system or the control device.

A classification unit in the form of a non-transitory machine-readable medium is preferable, on which program sections which can be read in and executed by a processor unit are stored in order to execute all the steps of a classification method according to at least one embodiment of the invention when the program sections are executed by the processor unit. In the form of this machine-readable medium, the classification unit can also be present as hardware, for example, as programmed EPROM.

Additional, particularly advantageous embodiments and developments of the invention will emerge from the claims and the description which follows, wherein the claims of one category of claim can also be developed analogously to the claims and parts of the description for another category of claim and in particular also individual features of various example embodiments and/or variants of new example embodiments and/or variants can be combined. In particular, the classification unit according to at least one embodiment of the invention can also be developed analogously to at least one embodiment of the method or parts of the description.

A method is preferred in which material index maps with location-dependent material index values are determined or provided, particularly as reference recordings. These material index maps comprise specific material index values MI for different areas of the recorded object.

Essentially, an appropriate material index value can be calculated from the spectral data in many different ways. A preferred option is described as an example hereinafter.

For example, if high kV recordings and low kV recordings of an object are present, it would be possible to calculate the material index value for individual areas (for example, pixels) according to the formula MI=(HV−LV)/(HV+LV), wherein "HV" is the value of the image area concerned (for example, pixel) in a high kV recording and "LV" the value of the image area concerned (for example, pixel) in a corresponding low kV recording. The spectral input data used for the calculation of a material index value, and/or material index map is naturally not limited to high kV and low kV recordings but other spectral image data can also be used which itself is only produced by way of calculation from the recorded data, in other words, for example, pseudo-monoenergetic images for various energies.

From the material index values, a material index map is therefore produced in which the material index value MI has a specific numerical value for each area. The material index values MI can thus also have location information regarding the position of the area in the object. The material index values MI may, for example, form a field of the form MI (x, y, z), which would constitute a preferred material index map.

In this case, the classification unit would be trained, preferably according to the principle of machine learning, using the location-dependent material index maps and/or such maps can be embodied in the context of the training. If the same object material index maps are produced for a series of reference recordings, after averaging, for example, a single material index map can be obtained which has error-corrected location-dependent material index values for all parts of the object. The location-dependent material index values determined from the spectral reference recordings are thus included as a parameter in a learning-based algorithm for material classification ("classification unit").

The spectral reference recordings of the reference recording set preferably comprise the following recordings:
  Recordings of an object with at least two different recording energies, for example, high kV, low kV, particularly in the form of two-spectra recordings or multi-energy computer tomography recordings, and/or
  Material-specifically decomposed receptacles, for example, two-material decomposition, three-material decomposition, and/or
  Mixed images, particularly with material information, and/or
  Material index maps with location-dependent material index values and/or
  A recording with a classification undertaken by a user of the object according to the various materials to be separated, for example, an identification of all the bones and all the vessels in the computed tomography images which he undertakes on the basis of his medical knowledge or other parameters, for example, laboratory results for the classification of kidney stones or gout, which is referred to as "Classified Gold Standard" hereinafter.

Preferably, at least one object classification is annotated in at least one of the reference recordings in addition to the annotation of the materials.

Preferably, the reference recordings comprise annotations of materials in the group calcium, iodine, water and uric acid and/or an object classification of the group of calcium-containing and iodine-containing contrast agent, calcified plaques, gout crystals, uric acid crystals and types of stone, for example, calcium-containing stones or uric acid-containing stones.

This has an advantage as the separation of calcium and iodine in CT angiographic recordings has been established as the clinical use of material separation by CT recordings with two or more X-ray energies, for example, for the automatic removal of the bones from the CT angiographic images or for the automatic removal of calcified plaques from the contrast agent-filled vessels. Furthermore, there is an advantage as clinical use can be made, for example, of the classification of kidney stones, for example in calcium-containing stones or in uric-acid containing stones, or the characterization of deposits in the joints, for example, gout, uric acid crystals or other deposits.

In the context of the aforementioned method, according to at least one embodiment of the invention, it is also preferable that a classification takes place using the material index map. Preferably, a spectral variable SG is calculated for an image area of the spectral image recording, for example, according to the formula SG=(HV−LV)/(HV+LV), wherein "HV" is again the value of the image area concerned (for example, pixels) for a high kV recording and "LV" the value of the image area concerned (for example, pixels) for a corresponding low kV recording. The calculated spectral variable SG can be compared with a material index value of the material index map in the corresponding image area. The material index value can serve as a limit value here. If the spectral variable SG is above this (SG>MI), a different material is classified than when SG is below this (SG<MI).

The location dependence of the material index value is a great advantage here as the spectral variable may depend on the position of the image pixel in the examination object. For example, different limit values may be necessary for abdominal recordings, depending on whether the center of the abdomen or the periphery is observed. A position-dependent limit value of the spectral variable relying heavily on the examination object, its variable, shape, etc. is advantageous for clean material separation.

As a further example embodiment of the aforementioned embodiment of the classification method according to the invention, materials in the group calcium, iodine, water, uric acid, soft tissue and iron are classified.

Object classification is preferably performed (if necessary, in addition) with categorization into classification objects in the group of calcium-containing and iodine-containing contrast agent, calcified plaques, gout crystals, uric acid crystals and types of stone, for example, calcium-containing stones or uric-acid containing stones.

An embodiment and/or development of the classification method according to at least one embodiment of the invention is also preferred which can alternatively or additionally be used for the control of a medical imaging system. This embodiment comprises the additional steps:

Provision of a Control Data Library.

Control data sets for a medical imaging system are stored in this control data library, which are linked by data technology with an erroneous material classification, for example, with error codes. The control data sets can particularly be configured such that the likelihood of erroneous material classification based on the image recordings produced is reduced, preferably minimized, when the control data set is used.

Selection of a Control Data Set.

The control data set is selected based on an erroneous classification of a material, in particular based on the location-dependent material index value of the material index map and/or an error code.

For example, an error code can be generated for the classification of a material which cannot occur in the examined area, or when the classification has values which deviate from predetermined limit values in an area due to image errors (for example, image noises).

By way of this error code, a particular control data set can be selected which is configured to perform a recording with determined recording energies which are specially designed to remedy the problem that occurs. However, a control data set which permits a recording to be performed from another recording angle can also be selected. Finally, however, it is also possible simply to select a control data record which initiates a new recording of the relevant area with the same recording parameters, in the hope that the noise was only for statistical reasons.

Use of the selected control data set.

The selected control data set is used for the renewed recording of the pattern (and/or examination object) of the examined image recording. In this way, the area of the object recorded in the original image recording is recorded again according to the selected control data set, resulting in a renewed, possibly improved image recording. A repetition of the entire examination due to erroneous image recordings is therefore unnecessary as upon detection of a reduction in quality, an image is immediately recorded using an optimized control.

Figure 1:
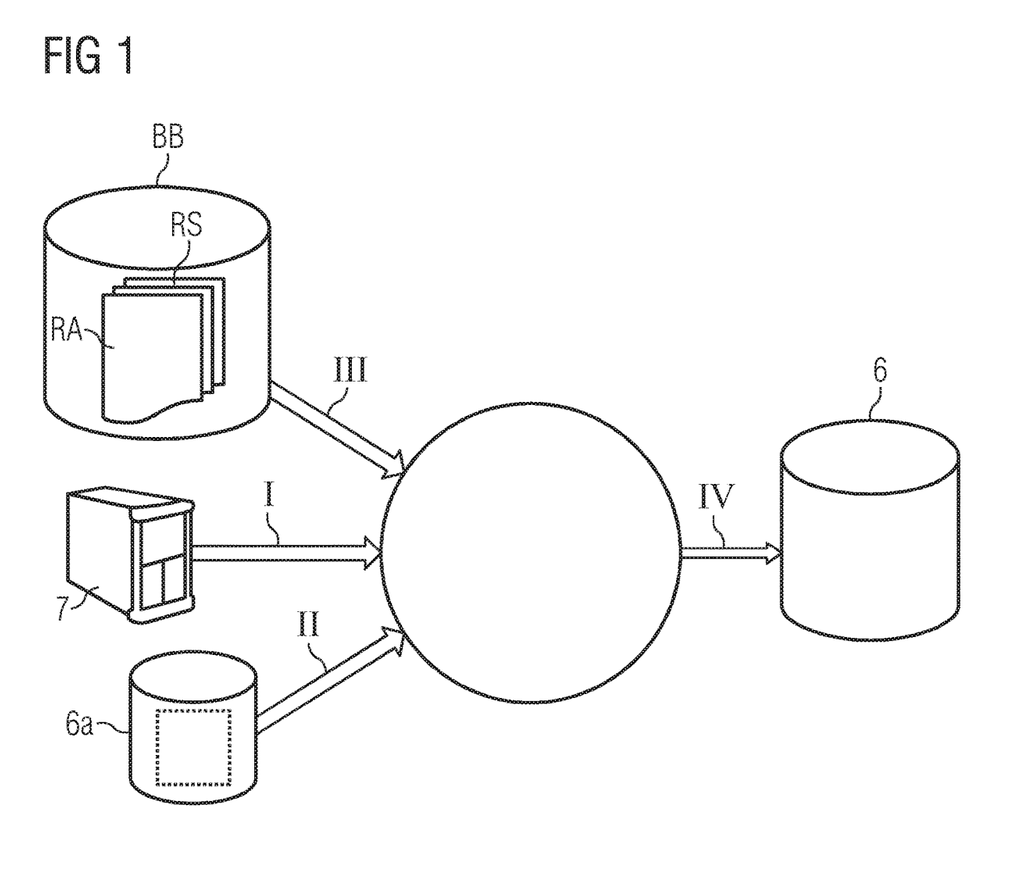
FIG. 1 shows a diagrammatic view of a first example embodiment of the method according to the invention for the production of a classification unit according to an embodiment of the invention.

FIG. 1 shows a diagrammatic view of a simple embodiment of the method according to the invention for the production of a classification unit according to an embodiment of the invention.

Figure 3:
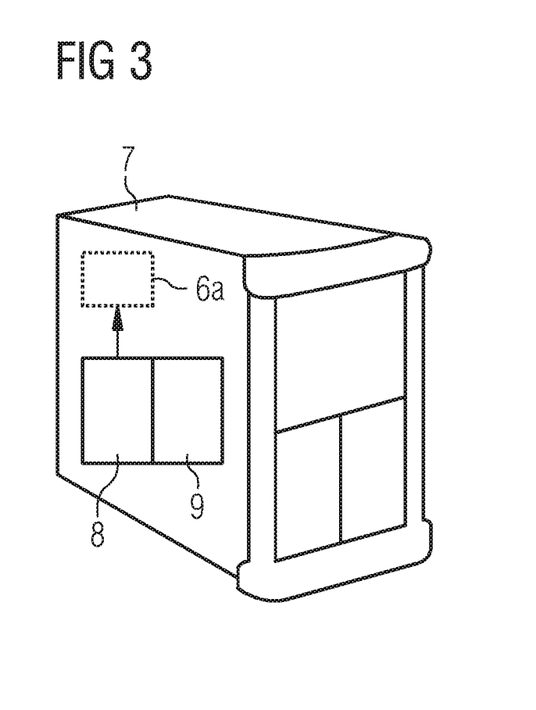
FIG. 3 shows a diagrammatic view of an example embodiment of a preferred learning computing device.

In step I, a learning computing device 7 is provided, wherein the learning computing device 7 is designed to detect graphic elements in image recordings and/or in image data of the image recordings via an algorithm (see also FIG. 3).

In step II, a start classification unit 6a is provided which is designed to be trained via machine learning, and basically represents the untrained classification unit 6. This start classification unit 6a is provided on or at the learning computing device 7, hence for example, connected by data technology to this learning computing device 7 as a database, as outlined here, or as data structure directly in this learning computing device 7.

In step III, an image data library BB is provided comprising a reference recording set RS from spectral reference recordings RA (these can be reference recordings RA which have been produced via a medical imaging system 1 or artificially generated reference recordings), wherein in the reference recordings RA materials M1, M2, M3 (see, for example, FIG. 4) are annotated.

The circle into which the three arrows with the designations I, II and III lead is here the initial state to which the three previous aspects have been supplied. The start classification unit 6a must now be trained to produce the classification unit 6.

In step VI, this training of the classification unit 6 takes place according to the principle of machine learning based on the detection of the materials M1, M2, M3 annotated in the reference recordings RA. An example of such training using location-dependent material index values MI1, MI2, MI3 is portrayed in FIG. 2.

Figure 2:
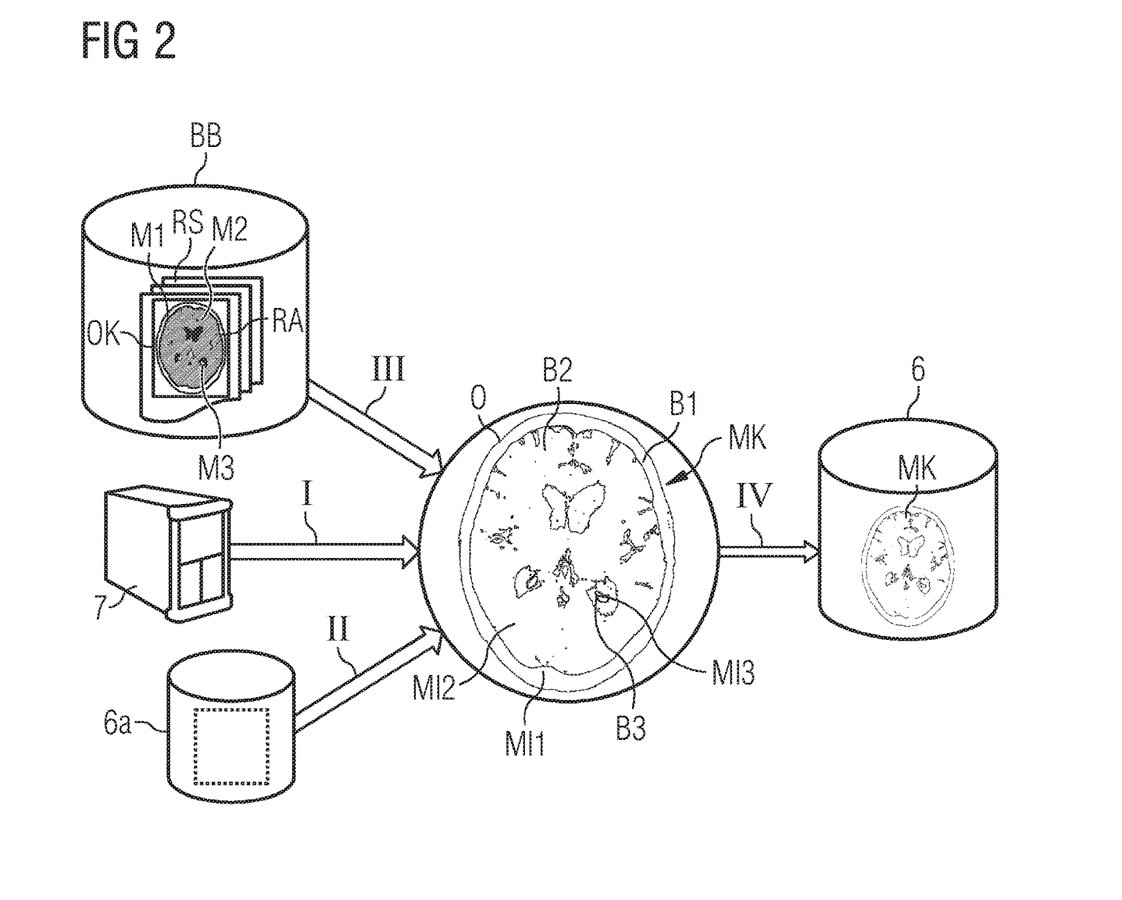
FIG. 2 shows a diagrammatic view of a second example embodiment of the method according to the invention for the production of a classification unit according to an embodiment of the invention with location-dependent material index values.

FIG. 2 shows a diagrammatic view of a preferred example embodiment of the method according to the invention for the production of a classification unit according to an embodiment of the invention. This figure represents an extension of FIG. 1 wherein the steps I, II and III are also performed here. In addition to the method according to FIG. 1, location-dependent material index values MI1, MI2, MI3 are included in the learning process here. These can be directly available in the reference recordings RA, for example, or be calculated from the image data of the reference recordings.

In step III, the provision of the image data library BB has been substantiated to the effect that the reference recording set RS has spectral reference recordings RA in which, apart from materials M1, M2, M3, object classifications OK (such as, for example, "kidney stone", "vessel wall", etc.) have also been annotated. The object classification OK shown here could be, for example, "cranial wall".

The circle of FIG. 2 shows a material index map MK, as could be obtained from the reference recordings RA. In addition to the materials M1, M2, M3 annotated in them, the reference recordings RA contain, for example, the spectral variables present in different image areas B1, B2, B3 in their image data. These spectral variables can be used to calculate material index values MI1, MI2, MI3.

In a simple case, it could be concluded from an annotated "iodine" for a pixel in an image area B3 and a spectral variable SG in the image data there (which, for example, can be calculated according to the above formula) that in the presence of this variable with this value SG, iodine is present in this image area B3, and this value SG can be stored as a limit value for iodine in the form of a material index value MI1. If this is done for a plurality of reference images in a plurality of different image areas B1, B2, B3, a map with specific (usually different) material index values MI1, MI2, MI3 can be produced for different image areas B1, B2, B3.

The initially calculated values SG therefore produce the material index values MI1, MI2, MI3 in the material index map MK which can be used as limit values in a subsequent classification. Different material index maps MK can be produced for different materials M1, M2, M3 in the course of training.

In this example, the training of the classification unit 6 in step IV is based on production of one or more material index maps MK.

FIG. 3 shows a diagrammatic view of a preferred learning computing device 7. This learning computing device 7 comprises a processor 8 and a data storage device 9 which are shown as blocks here. The data storage device 9 contains instructions which during their execution enable the processor 8 to record the reference recordings RA provided to the computing device, to detect annotated materials M1, M2, M3 in the reference recordings RA (see FIG. 2) as data objects, and to classify materials M1, M2, M3 in these image recordings and/or to produce material index maps MK and to train a start classification unit 6a, for example, according to an embodiment of the method according to an embodiment of the invention as shown in FIGS. 1 and 2.

Figure 4:
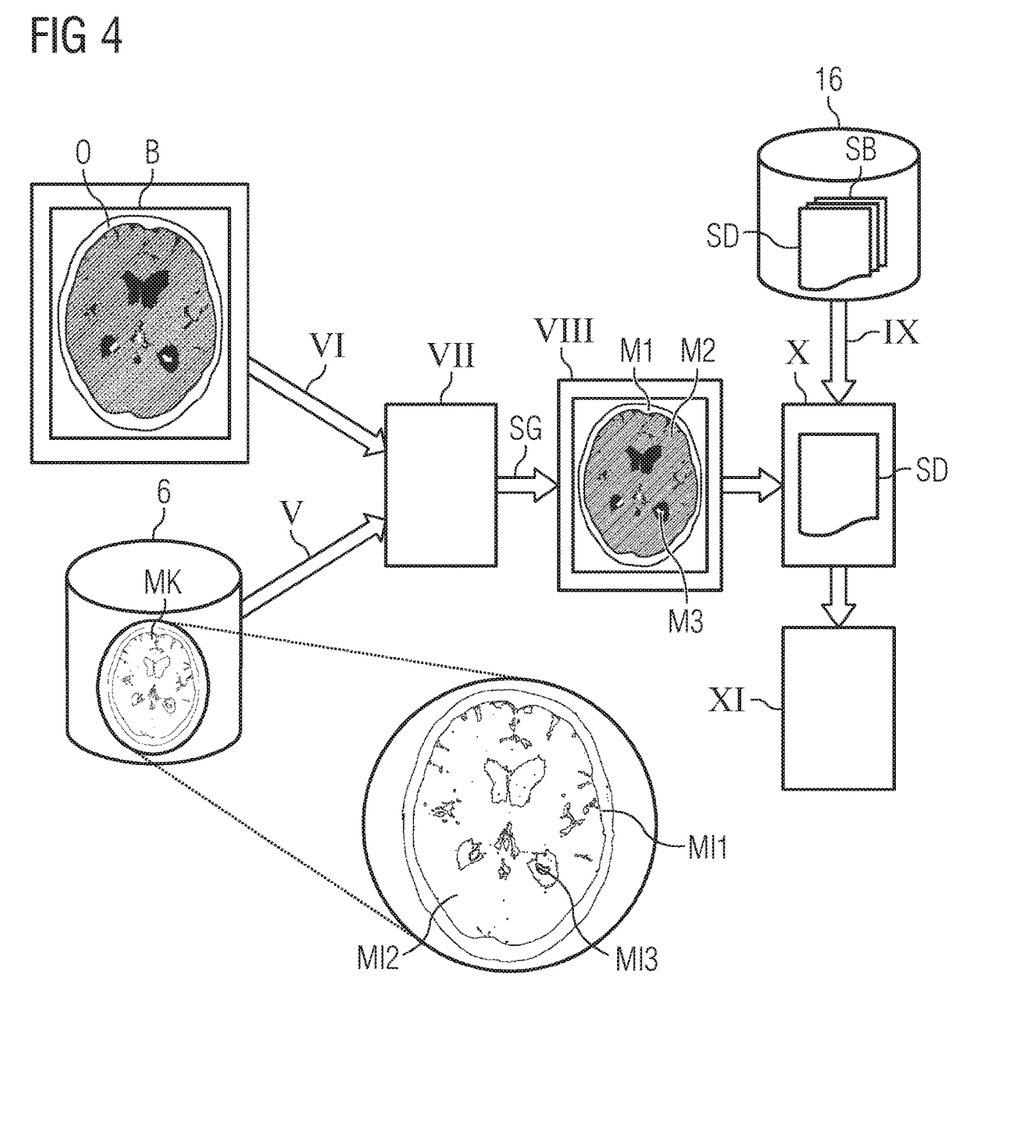
FIG. 4 shows a flow chart for a possible sequence of an example embodiment of a method according to the invention for the classification of materials.
Figure 5:
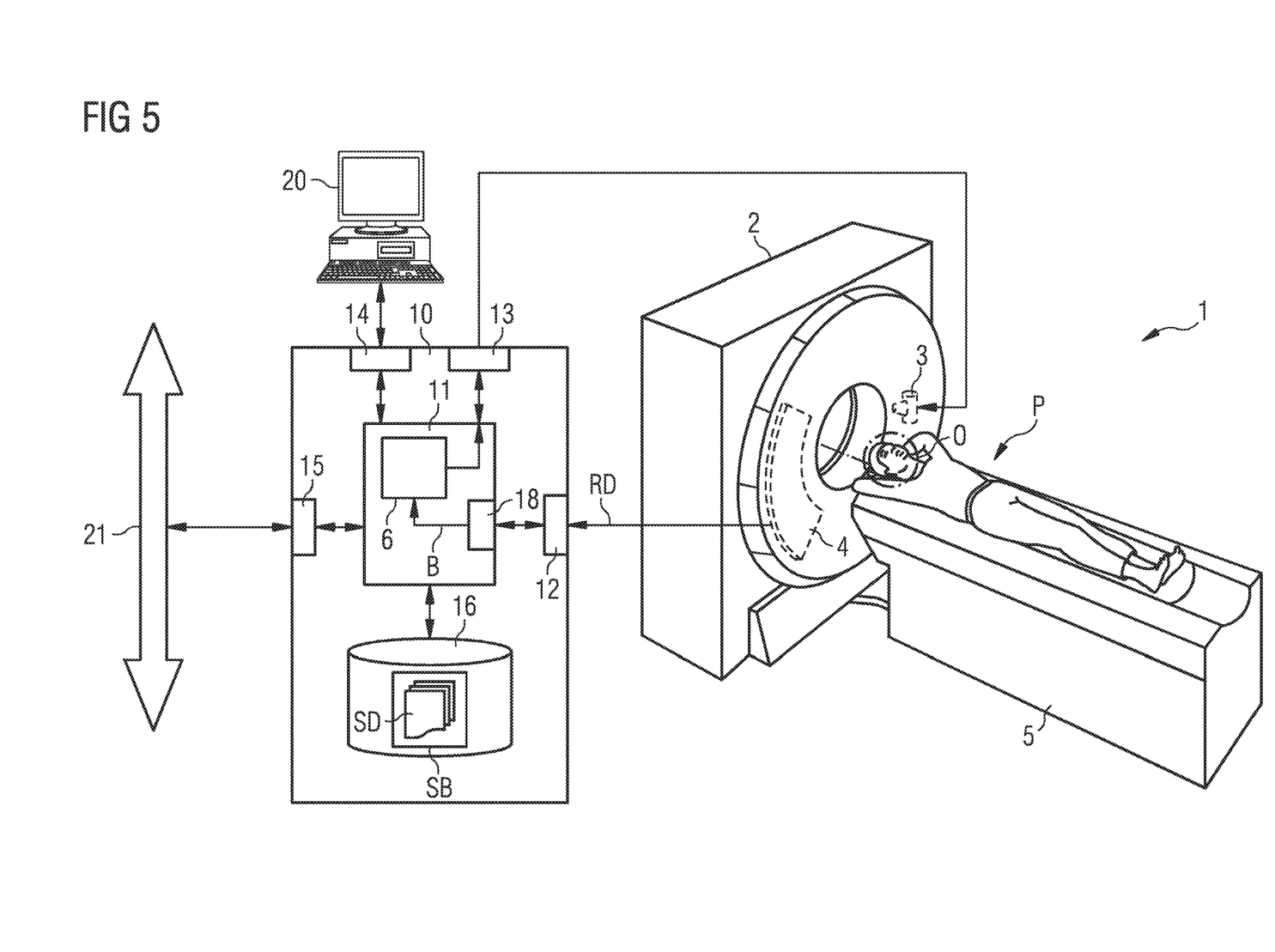
FIG. 5 shows a roughly diagrammatic view of a medical imaging system with an example embodiment of a control device according to the invention and classification unit for the performance of the method.

FIG. 4 shows a flow chart for a possible sequence of a method according to an embodiment of the invention for the classification of materials M1, M2, M3 in a medical image recording B currently to be examined and/or analyzed. This image recording B can be recorded, for example, via a medical imaging system 1, as shown in FIG. 5.

In step V, a classification unit 6 is provided which, for example, has been produced according to a method as shown in FIG. 1 or 2. The material index map MK in the classification unit 6 is intended to clarify that the classification unit 6 has been trained with location-dependent material index values MI1, MI2, MI3 and/or is equipped with a corresponding material index map MK. In addition to the presentation of the classification unit 6, the material index map MK for a CT slice image with location-dependent material index values MI1, MI2, MI3 is shown enlarged.

In step VI, an image recording B of an object currently to be analyzed is provided. This image recording B is, for example, a spectral recording produced via a medical imaging system 1. In this case, the image recording B is a tomography through a human skull.

In step VII, materials M1, M2, M3 are classified in the spectral image recording B, wherein in this example classification takes place using the material index map MK. In this case, a spectral variable SG is calculated for an image area (B1, B2, B3), for example, each individual pixel. This can take place, for example, with an image recording B comprising a recording at high X-ray energy ("High kV") and a recording at low X-ray energy ("Low kV") by calculating the formula SG=(HV−LV)/(HV+LV), wherein as aforementioned "HV" is the value of the pixel concerned at a high kV recording and "LV" is the value of the pixel concerned at a low kV recording. However, the spectral variable can also be defined in any other way desired. This spectral variable SG is then compared with a material index value MI1, MI2, MI3 from the material index map MK in such a way that the material index value MI1, MI2, MI3 of that area in the material index map MK which corresponds to the position of the pixel of the image recording B in the object O is selected.

In step VIII, automatic identification (annotation) of the determined materials M1, M2, M3 takes place, wherein a plurality of material index maps MK can be used for the classification of a plurality of different materials M1, M2, M3.

Up to this step, an example method for the pure classification of materials would be presented. With the automatic classification of materials M1, M2, M3 however, automatic control of an imaging medical system 1 may be included in addition or as an alternative to automatic identification, as illustrated by the further steps. For example, it may be the case that a material M1, M2, M3 is classified in an image area B1, B2, B3 which cannot occur in the area concerned or the detected object classification OK according to preset guidelines.

In the following (optional) step IX, a control data library SB is provided in which control data sets SD for a medical imaging system 1 are stored. These control data sets SD are linked to the results of the classification unit 6 in terms of data technology such that a control data set can be selected as a function of an incorrectly identified material M1, M2, M3 in an image area B1, B2, B3 of the image recording B.

In step X, a control data set SD is selected according to an incorrectly classified material M1, M2, M3 and/or an error code which has been generated on the basis of this incorrect classification.

In step XI, this selected control data set SD is used to control the imaging medical system 1 for the renewed recording of the pattern of the examined image recording B. As a result, the new image recording B can be recorded with new parameters which are specially selected to record the area of the object concerned according to special specifications for improved material classification (for example, the selection of other recording energies or another recording angle, or simply a renewed recording to compensate for statistical noise).

FIG. 5 shows a rough diagrammatic view of a dual energy computer tomography system 1 with a control device 10 which is designed to carry out a classification of materials and preferably also to carry out a learning process according to a method according to an embodiment of the invention.

The computer tomography system 1 (CT) conventionally has a scanner 2 with a gantry in which an X-ray source 3 rotates which in each case radiates a patient P with two beam energies which is pushed into a measurement space of the gantry by way of a bed 5 so that the radiation hits the detector 4 opposite the X-ray source 3 in each case. It is expressly pointed out that the example embodiment according to FIG. 5 is only an example of a CT and the invention can also be used on any other CTs desired. Frequently, for example, two X-ray sources 3 are used for two beam energies (dual source CT system).

Likewise, in the case of the control device 10 only the components which are essential for the explanation of embodiment of the invention or are helpful for understanding are shown. In principle, such CT systems and associated control devices are known to a person skilled in the art and therefore do not need to be explained in detail.

Likewise, embodiments of the invention can also be used on any other medical imaging systems desired.

A core component of the control device 10 here is a processor 11 on which different components are implemented in the form of software modules. Furthermore, the control device 10 has a terminal interface 14 to which a terminal 20 is connected, by way of which a user can operate the control device 10 and thus the computer tomography system 1. A further interface 15 is a network interface for connection to a data bus 21 in order to establish a connection to an RIS and/or PACS (RIS: Radiology Information System; PACS: Picture Archiving and Communication System). By way of this bus 21, for example, image data from image recordings can be forwarded or data (for example, reference recording sets) transferred.

By way of a control interface 13, the scanner 2 can be controlled by the control device 10, i.e. for example, the rotation speed of the gantry, the displacement of the patient bed 5 and the X-ray source 3 itself are controlled. By way of an acquisition interface 12, the raw data RD is read out from the detector 4.

Furthermore, the control device 10 has a storage unit 16 in which a control data library SB with control data sets SD is stored. The control data sets SD may, inter alia, be linked by data technology with an erroneous material classification and/or with a related error code.

A component on the processor 11 is an image data reconstruction unit 18 with which the desired image data B of the image recordings B of an object O are reconstructed from the raw data RD obtained by way of the data acquisition interface 12. This image data reconstruction unit 18 forwards the reconstructed image data B of an image recording B to a classification unit 6 in which materials M1, M2, M3 (see FIG. 4, for example) are first classified according to a method according to an embodiment of the invention.

In the event that it has been ascertained that a classified material M1, M2, M3 cannot occur at its position in the object O (for example, a kidney stone in the liver), a control data set SD is selected according to at least one predetermined classification error code from the control data library (SB) provided by the storage unit 16 and using the selected control data set SD, a new image recording B of the object O is produced in which preferably a classification of materials is likewise undertaken. In this manner, a set of image recordings B can be automatically produced in which materials have been correctly classified.

It is finally pointed out again that the method previously described in detail and the devices portrayed are merely example embodiments which may be modified by a person skilled in the art in many different ways without departing from the scope of the invention. Furthermore, the use of the indefinite article "a" and/or "an" does not preclude the relevant features also being present multiple times. Likewise, the terms "unit" and "module" do not preclude the relevant components consisting of a plurality of interacting partial components which may also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for training a classification unit for automatic classification of materials in a spectral medical image recording of an object, comprising:
provisioning a learning computing device, designed to recognize graphic elements in image recordings via an algorithm;
provisioning a start classification unit, on or at the learning computing device, trainable via machine learning;
provisioning a reference recording set including spectral reference recordings of the object, materials to be classified being annotated in the spectral reference recordings of the object; and
training the start classification unit according to at least one principle of machine learning, for automatic classification of materials in the spectral medical image recording of the object, using the materials annotated in the spectral reference recordings, wherein material index maps with location-dependent material index values are determined or provided, wherein the respective material index values for each of a plurality of areas has a specific numerical value wherein the start classification unit is trained according to the at least one principle of machine learning using the image recordings and is trained at least one of using and to embody material index maps.

2. The method of claim 1, wherein the spectral reference recordings of the reference recording set include at least one of:
recordings of an object with at least two different recording energies,
material-specifically decomposed recordings,
mixed images provided with material information,
material index maps with location-dependent material index values, and
a "Classified Gold Standard".

3. The method of claim 1 wherein, in addition to annotation of the materials, at least one object classification is annotated in the spectral reference recordings.

4. The method of claim 1, wherein the spectral reference recordings include at least one of
at least one annotation of materials including calcium, iodine, water or uric acid, and
at least one object classification including:
calcium-containing contrast agent,
iodine-containing contrast agent,
calcified plaque,
gout crystal,
uric acid crystal,
calcium-containing stone, or
uric-acid containing stone.

5. A classification unit for automatic classification of materials in a spectral medical image recording of an object, producible using the method of claim 1.

6. A learning computing device, comprising:
a processor; and
a data storage device storing program computer-readable instructions which, during execution, enable the processor to:
record reference recordings provided by the learning computing device as image data,
recognize materials in the reference recordings, and
train a start classification unit according to the method of claim 1.

7. A classification method, comprising:
provisioning or producing a classification unit trained via the method of claim 1;
provisioning a spectral medical image recording of an object;
classifying materials in the spectral medical image recording via the classification unit; and
identifying at least one of the materials classified and material-specific processing of the spectral medical image recording.

8. A classification method, comprising:
provisioning or producing a classification unit trained via a method for training the classification unit for automatic classification of materials in a spectral medical image recording of an object, including:
provisioning a learning computing device, designed to recognize graphic elements in image recordings via an algorithm,
provisioning the classification unit, on or at the learning computing device, trainable via machine learning,
provisioning a reference recording set including spectral reference recordings of the object, materials to be classified being annotated in the spectral reference recordings of the object, and
training the classification unit according to at least one principle of machine learning, for automatic classification of materials in the spectral medical image recording of the object, using the materials annotated in the spectral reference recordings;
provisioning a spectral medical image recording of an object;
classifying materials in the spectral medical image recording via the classification unit; and
identifying at least one of the materials classified and material-specific processing of the spectral medical image recording, wherein classifying takes place using at least one material index map, wherein, for an image area of the spectral image recording, a spectral variable is calculated and the calculated spectral variable is compared with a material index value of the material index map at a corresponding image area.

9. The classification method of claim 7, wherein materials including calcium, iodine, water, uric acid, soft tissue, and iron are classified during the classifying into classification objects in a group of calcium-containing contrast agent and iodine-containing contrast agent, calcified plaques, gout crystals, uric acid crystals and types of stone.

10. The classification method of claim 7, further comprising:
provisioning a control data library, storing control data sets for a medical imaging system;
selecting a control data set based on an erroneous classification of a material, and
using the control data set selected for a new recording of a pattern of the image recording.

11. A control device for control of a medical imaging system, designed for performance of the classification method of claim 7.

12. A medical imaging system comprising the control device of claim 11.

13. A non-transitory computer program product storing a computer program, directly loadable into a storage device of a computing system or a control device of a medical imaging system, including program sections to perform the method of claim 1 when the computer program is executed in the computing system or the control device.

14. A non-transitory machine-readable medium, storing program sections readable and executable by a processor, to perform the method of claim 1 when the program sections are executed by the processor.

15. The method of claim 2, wherein the spectral reference recordings of the reference recording set include at least one of:
recordings of an object with at least two different recording energies,
material-specifically decomposed recordings,
mixed images provided with material information,
material index cards with location-dependent material index values, and
a "Classified Gold Standard".

16. The method of claim 2 wherein, in addition to annotation of the materials, at least one object classification is annotated in the spectral reference recordings.

17. The method of claim 2, wherein the spectral reference recordings include at least one of
at least one annotation of materials including calcium, iodine, water or uric acid, and
at least one object classification including:
calcium-containing contrast agent,
iodine-containing contrast agent,
calcified plaque,
gout crystal,
uric acid crystal, calcium-containing stone, or uric-acid containing stone.

18. A non-transitory computer program product storing a computer program, directly loadable into a storage device of a computing system or a control device of a medical imaging system, including program sections to perform the method of claim 7 when the computer program is executed in the computing system or the control device.

19. A non-transitory machine-readable medium, storing program sections readable and executable by a processor, to perform the method of claim 7 when the program sections are executed by the processor.

20. A non-transitory machine-readable medium, storing program sections readable and executable by a processor, to perform the method of claim 8 when the program sections are executed by the processor.

21. The classification method of claim 8, wherein materials including calcium, iodine, water, uric acid, soft tissue, and iron are classified during the classifying into classification objects in a group of calcium-containing contrast agent and iodine-containing contrast agent, calcified plaques, gout crystals, uric acid crystals and types of stone.

22. A control device for control of a medical imaging system, designed for performance of the classification method of claim 8.

\* \* \* \* \*